United States Patent [19]
Kumar et al.

[11] Patent Number: 5,952,188
[45] Date of Patent: Sep. 14, 1999

[54] REUSABLE IMMOBILIZED MICROBIAL COMPOSITION USEFUL AS READY-TO-USE SEED INOCULUM IN BOD ANALYSIS

[75] Inventors: Rita Kumar; Anil Kumar; Alka Sharma; Sharad Vishwanath Gangal; Santosh Daya Ram Makhijani, all of Delhi, India

[73] Assignee: Council of Scientific & Industrial Research, New Dehli, India

[21] Appl. No.: 09/113,459

[22] Filed: Jul. 10, 1998

[51] Int. Cl.$^6$ .............. C12Q 1/54; C12Q 1/00; C12N 11/04; C12N 1/20
[52] U.S. Cl. .............. 435/14; 435/4; 435/30; 435/34; 435/38; 435/39; 435/42; 435/174; 435/182; 435/252.4; 435/817; 435/818; 210/609; 210/624; 436/62; 436/138
[58] Field of Search .............. 435/4, 14, 30, 435/34, 38, 39, 42, 174, 182, 252.4, 817, 818; 210/609, 624; 436/62, 138

[56] References Cited

U.S. PATENT DOCUMENTS

| | | | |
|---|---|---|---|
| 5,364,529 | 11/1994 | Morin et al. | 210/624 |
| 5,518,893 | 5/1996 | Park et al. | 435/29 |
| 5,531,960 | 7/1996 | Zelinka | 435/34 |
| 5,882,932 | 3/1999 | Yoon et al. | 435/62 |

OTHER PUBLICATIONS

Treatability, Toxicity and Biodegradability Test Methods: Biol. Rev. A. Kilroy, et al.: 1995: pp. 243–275.
Principles of Microbiology: Atlas, Ronald M.: Mosby Year Book: 1995: p. 579.
Biotechnology Letters: Anselmo, A.M. et al.: vol. 14: No. 3: Mar. 1992: pp. 239–244.
Biochemical Oxygen Demand from Water and Waste Water Technology: Mark J. Hammer: 1925: pp. 79–92.
Biotechnology Letters: Gijzen, H.J. et al.: vol. 10: No. 1: pp. 61–66.
Polyseed®BOD Seed Inoculum: Technical Data Sheet.
Evaluation of Manufactured Inocula for Use in the BOD Test, Water Research: G.D. Fitzmaurice and N.F. Gray: vol. 23: No. 5: pp. 655–567: 1989.
Removal and Recovery of CU(II) from Industrial Effluent by Immobilized Cells of Pseudomonas Putida II–II: Applied Microbiology and Biotechnology: P.O. Wong, et al: pp. 127–131: Spring–Verlag 1993.

*Primary Examiner*—Herbert J. Lilling
*Attorney, Agent, or Firm*—Ladas & Parry

[57] ABSTRACT

A reusable immobilized microbial composition is formulated. The formulated microbial composition comprises a synergistic mixture of the bacterial strains of *Enterobacter cloaca, Citrobacter amalonaticus, Pseudomonas aeruginosa, Yersinia enterocolitica, Klebsiella oxytoca, Enterobacter sakazaki* and *Serratia liquefaciens*. The formulated microbial composition is immobilized on an appropriate immobilizing agent to form beads. The said beads are tested as microbial seeding material for BOD analysis using Glucose Glutamic Acid (GGA) as a reference standard. The obtained BOD values by the formulated beads are compared with BOD values obtained by sewage as seeding material using synthetic samples as well as industrial effluents. The formulated microbial beads are ready-to-use as well as reusable seeding material in BOD analysis. The said beads can be reused up to five times with same efficacy.

16 Claims, No Drawings

REUSABLE IMMOBILIZED MICROBIAL COMPOSITION USEFUL AS READY-TO-USE SEED INOCULUM IN BOD ANALYSIS

FIELD OF THE INVENTION

The present invention relates to a reusable immobilized microbial formulation comprising a synergistic mixture of at least seven isolated bacterial strains present in equal proportion and a process for the preparation of said immobilized microbial formulation.

DESCRIPTION OF THE PRIOR ART

Biochemical Oxygen Demand (BOD) is one of the most widely used parameters for estimating the strength of water pollution. BOD-5 test measures the biodegradable organic matter present in waste waters. This determination involves the measurement of the dissolved oxygen during the biochemical oxidation of organic matter by the microorganisms at a standard duration and temperature. To ensure that meaningful results of BOD values are obtained, the sample must be suitably diluted with water so that adequate nutrients and oxygen will be available during the incubation period (APHA, 1995).

Besides this, the test sample in BOD test is 'seeded' with a bacterial culture for the biodegradation of organic matter. The conventional BOD test is based on naturally occurring microbes where, either raw sewage or treated effluent from waste-water treatment plant is used as a seeding material, which does not give reproducible BOD values. The degree of reproducibility of BOD test can not be defined precisely because of variations that occur in bacterial decomposition of various organic substances. Thus, in BOD analysis, bacterial seed represents a major variable and it can be controlled both quantitatively and qualitatively by the use of pure cultures (Fitzmaurice and Gray, 1989; Kilroy and Gray, 1995 and Hammer, 1975). This variation is probably due to source of seeding material (i.e. sewage which is collected from different places) wherein inadequate or variable microbial flora is present.

The reproducibility of the BOD values can be obtained by formulating a defined microbial composition as seeding material containing a uniform microbial population. Such formulations in the form of dehydrated seeding materials i.e. Polyseed and Bioseed (Fitzmaurice and Gray, 1989) have been developed in the USA and UK and are available in international market for use in BOD analysis. Polyseed is a registered trade mark of Polybac Corporation USA, consisting of a blend of specialized dehydrated microbial cultures in capsule form to provide a source of seeding material in BOD analysis. Polyseed is EPA accepted. Bioseed (trade name) is manufactured by International Biochemicals (UK) Ltd. and is being supplied as dehydrated seeding material in capsule form for BOD analysis. Bioseed from International Biochemicals, UK consists of a range of micro-organisms namely Pseudomonas, Nocardia, Streptomyces, Bacillus, and Micromonospora which are different from those of our composition. Though, these microbial compositions reduce the possibility of controversy in BOD results and make BOD analysis an easy, clean and convenient laboratory test, these microbial compositions need to be revived one day before performing the BOD analysis. The other drawbacks of the dehydrated seeding materials are that these dehydrated materials are not ready to use seeding material in BOD analysis and are not reusable. Whereas, the advantages of the present invention over the above technologies envisage a ready-to-use seeding material in BOD analysis. Besides, it is reusable seeding material (five times with the same efficacy) in BOD analysis. Due to the reusable property, immobilized microbial composition is more economical than the dehydrated seeding materials.

To avoid the discrepancies in BOD results as well as to obtain a ready-to-use seeding material in BOD test, in the present invention, a defined microbial composition is formulated as well as immobilized on a support to obtain a ready-to-use instant seeding material in BOD analysis. Immobilization of microorganisms leads to a reduction in cell growth and offers an easy-to-handle and ready-to-use material for many important industrial processes. Immobilized cells also offer promising potential for the improvement of efficiency of bioprocesses such as BOD analysis and biological waste-water treatment. The advantages of immobilized cells compared to free cells are that the immobilized cells can be used repeatedly and with ease of separation. Immobilized biocatalysts have also been used on an industrial scale for treating effluent containing phenolic compounds (Anselmo and Novail, 1992) as well as other toxicants (Wong et al., 1993; Gijzen et al, 1988).

SUMMARY OF THE INVENTION

For solving the aforementioned problem, the inventors have realized that there exists a need to provide a process for the development of a ready-to-use, low cost and reusable seeding material for BOD test.

The present invention relates to a reusable immobilized microbial formulation and a process for the preparation of the immobilized microbial composition useful as ready-to-use seed inoculum for the determination of Biochemical Oxygen Demand (BOD), more particularly to reproducibility of results as well as reusability of seed inoculum in BOD test and immobilized microbial composition thereby. The immobilized formulated microbial mixture comprises cultures of the following bacteria: (a) *Enterobacter cloaca* (b) *Citrobacter amalonaticus* (c) *Pseudomonas aeruginosa* (d) *Yersinia enterocolitica* (e) *Klebsiella oxytoca* (f) *Enterobacter sakazaki* and (g) *Serratia liquefaciens* which are pre-tested for BOD analysis individually. The formulated microbial composition is obtained by inoculating a suspension of these bacteria individually, incubating at 37° C., mixing all bacteria in equal proportions based on optical density and centrifuging. The resultant pellet is mixed with a solution of an immobilizing agent, sodium alginate and adding the resultant slurry to 0.1 M $CaCl_2$ to form beads.

Accordingly, another aspect of the present invention, provides a process for the production of novel immobilized formulated microbial mixture useful as seed inoculum in BOD analysis which is reusable five times with same efficacy.

DETAILED DESCRIPTION OF THE INVENTION

The composition provided according to the present invention contains bacteria comprising:

| | | | |
|---|---|---|---|
| 1. | Enterobacter cloaca | CBTCC/Micro/1 | (Corresponding ATCC No. 29893) |
| 2. | Citrobacter amalonaticus | CBTCC/Micro/2 | (Corresponding ATCC No. 25406) |
| 3. | Pseudomonas aeruginosa | CBTCC/Micro/3 | (Corresponding ATCC No. 49622) |
| 4. | Yersinia enterocolitica | CBTCC/Micro/4 | (Corresponding ATCC No. 27739) |

-continued

| | Cultures | | Accession number | Corresponding ATCC No. |
|---|---|---|---|---|
| 5. | Klebsiella oxytoca | | CBTCC/Micro/5 | (Corresponding ATCC No. 15764) |
| 6. | Enterobacter sakazaki | | CBTCC/Micro/6 | (Corresponding ATCC No. 12868) |
| 7. | Serratia liquefaciens | | CBTCC/Micro/7 | (Corresponding ATCC No. 25641) | which facilitates giving uniform reproducible results in BOD estimations performed at any place. Above microorganisms are deposited at Centre for Biochemical Technology Culture Collection (CBTCC) designated as stated above and will be made available to public on request as per normal official procedures. The composition may contain the bacteria, in a preferred embodiment of the invention, in uniform amounts. Moreover, the composition of the present invention will be ready to use instead of preparing each time which involves collecting the sewage everytime from treatment plants.

The composition of the present invention is useful in determining the strength of water pollution, waste loadings to treatment plants and evaluating the efficiency of such treatment.

The bacterial cultures of the above composition can be isolated from sewage such as sewage samples collected from Dhirpur Coronation plant near Mukherjee Nagar, Delhi. Sewage is homogenized for 2 minutes and suspended in gram negative broth. Incubation is carried out for 24 hours. Cultures are plated on Mac Conkey's agar. A mixture of lactose and non-lactose fermentors are isolated. Colonies are mixed on a vortex mixer and all the cultures are isolated in pure cultures after several subcultures.

The pure cultures are checked for the gram reaction. All the gram negative cultures are maintained as stock cultures. The cultures are further identified by the rapid identification schemes.

The cultures which are gram negative bacilli and catalase positive, are included. Seven pure cultures as indicated below which are included in the composition were identified by the classification scheme of Edwards and Ewing (1972) along with designated changes by Centre for Disease Control (CDC), Atlanta, 1978.

| | Cultures | Accession number | Corresponding ATCC No. |
|---|---|---|---|
| 1. | Enterobacter cloaca | CBTCC/Micro/1 | (29893) |
| 2. | Citrobacter amalonaticus | CBTCC/Micro/2 | (25406) |
| 3. | Pseudomonas aeruginosa | CBTCC/Micro/3 | (49622) |
| 4. | Yersinia enterocolitica | CBTCC/Micro/4 | (27739) |
| 5. | Klebsiella oxytoca | CBTCC/Micro/5 | (15764) |
| 6. | Enterobacter sakazaki | CBTCC/Micro/6 | (12868) |
| 7. | Serratia liquefaciens | CBTCC/Micro/7 | (25641) |

The immobilization technique of formulated microbial mixture of the present invention is carried out by inoculating the individual strains of the above mentioned bacteria separately in a nutrient broth. All the cultures are incubated preferably at 37° C. for approximately 24 hrs. in an incubator shaker. For gentle shaking, the incubator shaker is maintained at an appropriate rpm, preferably at 75 rpm. After sufficient growth is obtained, the bacterial cells from these individual cultures are taken in the required quantity and then mixed for preparing the microbial composition. The resultant microbial composition is centrifuged at appropriate rpm, preferably at 10,000 rpm for a period of approximately 30 minutes. The resultant pellet is washed by dissolving in a minimum quantity of distilled water and recentrifuged at appropriate rpm, preferably at 10,000 rpm. for a period of approximately 30 minutes. During centrifugation, the temperature is maintained preferably at 4° C. The pellets thus obtained, is immobilized by entrapping them in immobilizing agent such as calcium alginate gel. The immobilization can be affected by mixing the pellets using 2% sodium alginate solution and the resultant slurry is pumped into a stirred 0.1 M $CaCl_2$ solution. The cell slurry is intruded as discrete droplets so as to form beads of appropriate size. The beads thus formed, are left in 0.1 M calcium chloride solution for approximately 3 hours and later washed with double distilled water. The immobilized microbial beads are stored in 0.05 M $CaCl_2$ solution at a temperature preferably 4° C.

The beads so obtained can be used as seed inoculum in varying quantities for BOD estimation using Glucose-Glutamic Acid (GGA) as a reference standard by the method described in the Standard method for the Examination of Water and Wastewaters 17$^{th}$ edition, American Public Health Association, Washington DC (1989). After optimization of the quantity of beads in the BOD analysis, the beads were used as seeding material for BOD estimation of various synthetic samples as well as industrial effluents.

Accordingly, the invention provides a reusable immobilized microbial formulation comprising a synergistic mixture of at least the following isolated bacterial strains present in equal proportion (equal concentration) useful for Biological Oxygen Demand (BOD) analysis:

| | | | |
|---|---|---|---|
| 1. | Enterobacter cloaca | CBTCC/Micro/1 | (Corresponding ATCC No. 29893) |
| 2. | Citrobacter amalonaticus | CBTCC/Micro/2 | (Corresponding ATCC No. 25406) |
| 3. | Pseudomonas aeruginosa | CBTCC/Micro/3 | (Corresponding ATCC No. 49622) |
| 4. | Yersinia enterocolitica | CBTCC/Micro/4 | (Corresponding ATCC No. 27739) |
| 5. | Klebsiella oxytoca | CBTCC/Micro/5 | (Corresponding ATCC No. 15764) |
| 6. | Enterobacter sakazaki | CBTCC/Micro/6 | (Corresponding ATCC No. 12868) |
| 7. | Serratia liquefaciens | CBTCC/Micro/7 | (Corresponding ATCC No. 25641) |

The invention further provides a process for the preparation of immobilized microbial formulation which comprises:

(a) isolating a range of bacterial strains of at least *Enterobacter cloaca, Citrobacter amalonaticus, Pseudomonas aeruginosa, Yersinia enterocolitica, Klebsiella oxytoca, Enterobacter sakazaki* and *Serratia liquefaciens* from sewage collected from treatment plants by known methods (see: Principles of Microbiology ed. James M. Smith (Mosby Publishing, 1995) and Cappuccino, G. James and Sherman, N. Technique for isolation of pure cultures In Microbiology, A laboratory manual, IV Editors, The Benjamins/Cummings publishing Company, Inc., 13–15, 1996

(b) culturing the strains on nutrient media to obtain pure cultures;

(c) testing the individual pure bacterial culture for BOD analysis and recording BOD values obtained from individual strains;

(d) verifying the BOD values obtained with glucose-glutamic acid as a reference standard;

(e) comparing the BOD values using the bacterial strains as seeding material with that of the observed BOD values using domestic sewage as seeding material, collected from sewage treatment plants;

(f) selecting the bacterial strains which have BOD values equal to or more than the BOD values of sewage as observed in step (e);

(g) preparing mixtures of selected bacterial strains;

(h) testing the mixtures of selected bacterial strains by comparing their BOD values with those of domestic sewage;

(i) selecting the mixtures having optimum BOD values;

(j) inoculating the mixture of the bacterial strains obtained in step (i), individually;

(k) incubating the bacterial strains and growing the incubated strains;

(l) mixing the incubated strains from step (k) in equal proportions on the basis of optical density values;

(m) centrifuging the resultant suspension to obtain pellets, washing the collected pellet with distilled water and suspending the pellet in a solution of an appropriate immobilizing agent;

(n) adding the resultant slurry to an appropriate polymerizing agent to form beads and curing the resultant beads by known methods;

(o) hardening the beads by leaving the said beads in 0.1 M to 0.2 M $CaCl_2$ solution for approximately 3 hrs.;

(p) storing the prepared immobilized microbial beads in a concentration range of 0.05 M to 0.2 M $CaCl_2$ solution at a temperature preferably less than or equal to 4° for longer use;

(q) testing formulated beads for BOD analysis using GGA as a reference standard;

(r) comparing BOD values using the formulated beads with BOD values of those obtained with sewage as seeding material using synthetic samples;

(s) testing the beads for BOD analysis using different industrial samples;

(t) washing the used beads three times with distilled water;

(u) storing the used beads at about 4° C. for further use at least for five times.

In an embodiment of the invention, the formulated microbial composition is obtained by inoculating a suspension of the bacteria selected from a group consisting of (a) *Enterobacter cloaca* (b) *Citrobacter amalonaticus* (c) *Pseudomonas aeruginosa* (d) *Yersinia enterocolitica* (e) *Klebsiella oxytoca* (f) *Enterobacter sakazaki* (g) *Serratia liquefaciens*, individually.

In another embodiment of the invention, the individual strains of the above mentioned bacteria are inoculated separately in a nutrient broth.

In a further embodiment of the invention, the incubation of bacterial strains is carried out by gentle agitation at approximately 75–100 rpm.

In an embodiment of the invention, the growth of incubated bacterial strains is carried out at a temperature ranging between 35° C.–40° C. for a period of 16–24 hours.

In an embodiment of the invention, the individual strains of bacteria are mixed in equal proportions.

In a further embodiment of the invention, the resultant microbial composition is centrifuged at appropriate rpm preferably at 8,000 to 12,000 rpm for a period of approximately 20 to 30 minutes.

In yet another embodiment of the invention, the resultant pellet is washed by dissolving in an appropriate quantity of distilled water and recentrifuging at an appropriate rpm in the range of 8,000 to 12,000 rpm for a period of approximately 20 to 30 minutes at a temperature less than or equal to 4° C.

In an embodiment of the invention, the resultant pellet obtained is immobilized by entrapping in sodium alginate as an immobilizing agent.

In one of the embodiments of the invention, the resultant slurry used is pumped into a stirred $CaCl_2$ solution with concentration ranging between 0.05–0.2 M.

In an embodiment of the invention, wherein the cell slurry is intruded as discrete droplets so as to form beads of appropriate size.

In a further embodiment of the invention, the beads are washed with double distilled water to remove extra $CaCl_2$ solution.

In an embodiment of the invention, the immobilized microbial beads formed are stored in 0.05 M to 0.2 M $CaCl_2$ solution at a temperature preferably less than or equal to 4° C. for longer use.

The examples provided below are given by way of illustration of the invention and therefore, should not be construed to limit the scope of invention.

EXAMPLE I

Two loops from agar plates of *Enterobacter cloaca, Citrobacter amalonaticus, Pseudomonas aeruginosa, Yersinia enterocolitica, Klebsiella oxytoca, Enterobacter sakazaki* and *Serratia liquefaciens* were inoculated separately in 500 ml of nutrient broth. All the cultures were incubated at 37° C. for 24 hrs. in an incubator shaker at 75 rpm. After incubation, optical density was measured at 650 nm. Optical density of all the bacteria was maintained to about 0.5 either by diluting or concentrating the bacterial suspension. All bacterial suspensions were mixed thoroughly and centrifuged at 8,000 rpm for 30 minutes at 4° C. The pellet was washed by dissolving it in small volume of distilled water and recentifuged at 8,000 rpm for 30 minutes at 4° C.

The microbial composition prepared as described above was mixed with 1% sodium alginate solution. The resultant slurry was pumped into a stirred 0.05 M calcium chloride solution. The beads thus formed, were left in 0.1 M calcium chloride solution for 3 hrs. and later washed with double distilled water. The immobilized microbial beads were stored in 0.05 M calcium chloride solution at 4° C. The beads were non-spherical, less stable.

EXAMPLE II

Two loops from agar plates of *Enterobacter cloaca, Citrobacter amalonaticus, Pseudomonas aeruginosa, Yersinia enterocolitica, Klebsiella oxytoca, Enterobacter sakasaki* and *Serratia liquefaciens* were inoculated separately in 500 ml of nutrient broth. All the cultures were incubated at 37° C. for 24 hrs. in an incubator shaker at 100 rpm. After incubation, optical density was measured at 650 nm. Optical density of all the bacteria was maintained to about 0.5 either by diluting or concentrating the bacterial suspension. All bacterial suspensions were mixed thoroughly and centrifuged at 10,000 rpm for 30 minutes at 4° C. The pellet was washed by dissolving it in small volume of distilled water and recentifuged at 10,000 rpm for 30 minutes at 4° C.

The microbial composition was mixed with 1.5% sodium alginate solution. The resultant alginate bacterial suspension was pumped drop-wise into a stirred 0.1M calcium chloride solution. The beads thus formed, were left in 0.1M $CaCl_2$ solution for 3 hrs. and later washed with double distilled water. The microbial beads were stored in 0.05 M $CaCl_2$ solution at 4° C. The beads obtained were slightly spherical and less stable.

EXAMPLE III

Two loops from agar plates of *Enterobacter cloaca, Citrobacter amalonaticus, Pseudomonas aeruginosa, Yersinia enterocolitica, Klebsiella oxytoca, Enterobacter sakazaki* and *Serratia liquefaciens* were inoculated separately in 500 ml of nutrient broth. All the cultures were incubated at 37° C. for 24 hrs. in an incubator shaker at 75 rpm. After incubation, optical density was measured at 650 nm. Optical density of all the bacteria was maintained to about 0.5 either by diluting or concentrating the bacterial suspension. All bacterial suspensions were mixed thoroughly and centrifuged at 12,000 rpm for 30 minutes at 4° C. The pellet was washed by dissolving it in small volume of distilled water and recentifuged at 12,000 rpm for 30 minutes at 4° C.

The microbial composition was mixed with 2.0% sodium alginate solution. The resultant alginate bacterial suspension was pumped drop-wise into a stirred 0.15M calcium chloride solution. The beads thus formed, were left in 0.1 M calcium chloride solution for 3 hrs. and later washed with double distilled water. The immobilized microbial beads were stored in 0.05 M calcium chloride solution at 4° C. The beads thus formed were spherical, stable and porous.

EXAMPLE IV

Two loops from agar plates of *Enterobacter cloaca, Citrobacter amalonaticus, Pseudomonas aeruginosa, Yersinia enterocolitica, Klebsiella oxytoca Enterobacter sakazaki* and *Serratia liquefaciens* were inoculated separately in 500 ml of nutrient broth. All the cultures were incubated at 37° C. for 24 hrs. in an incubator shaker at 75 rpm. After incubation, optical density was measured at 650 run. Optical density of all the bacteria was maintained to about 0.5 either by diluting or concentrating the bacterial suspension. All bacterial suspensions were mixed thoroughly and centrifuged at 10,000 rpm for 30 minutes at 4° C. The pellet was washed by dissolving it in small volume of distilled water and recentifuged at 10,000 rpm for 30 minutes at 4° C.

The microbial composition was mixed with 2.5% sodium alginate solution. The microbial beads were prepared by using 0.2 M calcium chloride solution. The beads thus formed, were left in 0.1 M calcium chloride solution for 3 hrs. and later washed with double distilled water. The immobilized microbial beads were stored in 0.05 M calcium chloride solution at 1C. The beads thus formed were hard and less porous.

EXAMPLE V

Two loops from agar plates of *Enterobacter cloaca, Citrobacter amalonaticus, Pseudomonas aeruginosa, Yersinia enterocolitica, Klebsiella oxytoca, Enterobacter sakazaki* and *Serratia liquefaciens* were inoculated separately in 500 ml of nutrient broth. All the cultures were incubated at 37° C. for 24 hrs. in an incubator shaker at 75 rpm. After incubation, optical density was measured at 650 run. Optical density of all the bacteria was maintained to about 0.5 either by diluting or concentrating the bacterial suspension. All bacterial suspensions were mixed thoroughly and centrifuged at 10,000 rpm for 30 minutes at 4° C. The pellet was washed by dissolving it in small volume of distilled water and recentifuged at 10,000 rpm for 30 minutes at 4° C.

The microbial composition was mixed with 3.0% sodium alginate solution. The resultant mix was pumped into a stirred 0.1 M calcium chloride solution. The beads thus formed, were left in 0.1 M calcium chloride solution for 3 hrs. and later washed with double distilled water. The immobilized microbial beads were stored in 0.2 M calcium chloride solution at 4° C. The beads were more hard and less porous.

EXAMPLE VI

Beads prepared from microbial composition using 2.0% sodium alginate (stable and porous beads) were used in BOD analysis using 2% solution of Glucose-Glutamic Acid (GGA), a reference standard which contains each of 150 mg of Glucose as well as Glutamic Acid. Table 1 shows BOD values of GGA using different quantities of beads as well as sewage as seeding materials. The sample was analyzed at five different times.

TABLE 1

Standardization of optimum quantity of microbial beads for BOD estimation with 2% GGA

| | BOD value ($O_2$, mg/l) using different quantities of beads and sewage | | | | |
|---|---|---|---|---|---|
| Replicates | 2 beads | 4 beads | 8 beads | 12 beads | Sewage |
| 1 | 170 | 194 | 195 | 195 | 188 |
| 2 | 173 | 199 | 198 | 201 | 190 |
| 3 | 176 | 190 | 189 | 191 | 187 |
| 4 | 179 | 196 | 196 | 198 | 191 |
| 5 | 172 | 189 | 191 | 190 | 193 |
| Means | 174 | 193.6 | 193.8 | 195 | 189.8 |
| Range | 9 | 10 | 9 | 10 | 6 |
| S.D. | 3.535 | 4.159 | 3.701 | 4.636 | 2.387 |
| % CV | 2.03 | 2.14 | 1.9 | 2.3 | 1.2 |

BOD values of GGA using four or more than four beads were comparable with the values obtained with those by sewage. Based on this observation, four microbial beads were used for further BOD analysis.

EXAMPLE VII

Microbial beads in parallel with sewage were used for BOD determination of different synthetic samples namely Peptone, Glucose, L-Glutamic acid & Citric acid. A stock solution (0.03%) of each of these synthetic samples was prepared. For BOD estimation, 2% solutions of these stocks were used.

Table 2 represents BOD values of all the above four synthetic samples. The BOD analysis was carried out at five different times and results were compared with those obtained with sewage as seeding material.

TABLE 2

BOD estimation of synthetic samples with immobilized beads as well as sewage

BOD values ($O_2$, mg/l) of synthetic samples

| Replicates | Glucose | | Peptone | | Glutamic Acid | | Citric acid | |
|---|---|---|---|---|---|---|---|---|
| | Beads | Sewage | Beads | Sewage | Beads | Sewage | Beads | Sewage |
| 1. | 195 | 190 | 215 | 182 | 168 | 164 | 153 | 156 |
| 2. | 190 | 181 | 194 | 171 | 151 | 152 | 160 | 168 |
| 3. | 185 | 175 | 185 | 180 | 176 | 157 | 170 | 166 |
| 4. | 182 | 179 | 194 | 175 | 159 | 157 | 155 | 152 |
| 5. | 195 | 184 | 191 | 178 | 172 | 161 | 173 | 178 |
| Mean | 189 | 182 | 196 | 177 | 165 | 158 | 166 | 164 |
| Range (Max.–Min.) | 20 | 15 | 30 | 15 | 30 | 15 | 25 | 25 |
| S.D. | 5.9 | 5.6 | 11.3 | 4.3 | 10.1 | 4.5 | 8.9 | 10.3 |
| % CV | 3.1 | 3.1 | 5.8 | 2.4 | 6.1 | 2.9 | 5.5 | 6.3 |

Fairly comparable BOD values were obtained by using immobilized microbial beads as well as sewage as seeding materials.

EXAMPLE VIII

Table 3 & 4 represents the BOD values of various industrial effluents namely paper & pulp, bioproducts, distillery, pharmaceutical, soft drink and vegetable oil industries. The samples were collected at five different times for BOD analysis in order to check the reproducibility and repeatability. For statistical analysis of the data, five replicates of each sample were analyzed.

Table 3 represents the BOD analysis of paper & pulp, bioproducts and distillery industrial effluents by using immobilized microbial beads as well as sewage as a seeding materials.

TABLE 3

BOD values of three different industrial samples using beads as well as sewage as a seeding materials BOD values ($O_2$, mg/l) of industrial samples

| Replicates | Paper & Pulp | | Bio-products | | Distillery | |
|---|---|---|---|---|---|---|
| | Beads | Sewage | Beads | Sewage | Beads | Sewage |
| 1. | 1,900 | 1,820 | 9,900 | 8,300 | 22,200 | 20,100 |
| 2. | 1,840 | 1,700 | 10,900 | 6,700 | 22,850 | 19,320 |
| 3. | 1,808 | 1,790 | 10,830 | 7,790 | 23,720 | 20,250 |
| 4. | 1,970 | 1,840 | 10,200 | 8,100 | 23,630 | 19,180 |
| 5. | 1,910 | 1,880 | 10,640 | 8,280 | 22,470 | 20,870 |
| Mean | 1,886 | 1,806 | 10,429 | 7,834 | 23,174 | 19,944 |
| Range | 162 | 180 | 1,000 | 1,600 | 1,250 | 1,690 |
| S.D. | 63.3 | 67.3 | 429.6 | 666.1 | 526.1 | 697.9 |
| % CV | 3.4 | 3.7 | 4.1 | 8.5 | 2.3 | 3.5 |

BOD values of paper & pulp industrial effluent by using immobilized microbial beads as well as sewage were found to be reasonably comparable. On the other hand, BOD values of bio-products and distillery industrial effluents by using immobilized beads were higher than those obtained with sewage which indicates better performance of immobilized microbial beads as seeding material in BOD analysis.

BOD values of pharmaceutical, soil drink and vegetable oil industrial effluents using immobilized microbial beads and sewage as seeding material are presented in Table 4.

TABLE 4

BOD values of three different industrial samples using beads as well as sewage as a seeding materials BOD values ($O_2$, mg/l) of industrial samples

| Replicates | Pharmaceutical | | Soft drink | | Vegetable Oil | |
|---|---|---|---|---|---|---|
| | Beads | Sewage | Beads | Sewage | Beads | Sewage |
| 1. | 1,600 | 1,250 | 3,740 | 3,740 | 3,470 | 3,280 |
| 2. | 1,670 | 1,430 | 3,620 | 3,660 | 3,320 | 3,330 |
| 3. | 1,630 | 1,310 | 3,780 | 3,520 | 3,410 | 3,370 |
| 4. | 1,680 | 1,400 | 3,720 | 3,600 | 3,390 | 3,170 |
| 5. | 1,670 | 1,360 | 3,700 | 3,430 | 3,510 | 3,210 |
| Mean | 1,650 | 1,350 | 3,712 | 3,590 | 3,420 | 3,264 |
| Range | 80 | 150 | 200 | 350 | 210 | 250 |
| S.D. | 33.9 | 71.8 | 59.3 | 120.4 | 73.5 | 95.8 |
| % CV | 2.1 | 5.3 | 1.9 | 3.4 | 2.1 | 2.9 |

Table indicates that BOD values of soft drink as well as vegetable oil industrial effluent by using immobilized microbial beads and sewage as seeding materials were comparable while BOD values of pharmaceutical industrial effluent by using immobilized microbial beads were higher than those obtained using sewage as seeding material.

EXAMPLE IX

To check the reusability of prepared microbial beads, BOD analysis of reference GGA solution was carried out by using the same set of beads for five different times as shown in Table 5. On the other hand, fresh sewage was used for each BOD estimation for the comparison of the results. BOD values of reused beads thus obtained were compared with the sewage. The results with reused beads as seeding material in BOD analysis were found to be comparable with those of sewage when beads were used five times.

TABLE 5

Reusability studies of beads using GGA

BOD values (O₂ mg/l) of beads reused up to 5 times

|  | I Time | | II Time (After 1 weeks) | | III Time (After 2 weeks) | | IV Time (After 3 weeks) | | V Time (After 4 weeks) | |
| --- | --- | --- | --- | --- | --- | --- | --- | --- | --- | --- |
|  | Beads | Sewage | Beads | Sewage | Beads | Sewage | Beads | Sewage | Beads | Sewage |
| 1. | 185 | 186 | 189 | 177 | 184 | 184 | 179 | 186 | 182 | 181 |
| 2. | 208 | 191 | 213 | 187 | 203 | 194 | 204 | 193 | 202 | 174 |
| 3. | 210 | 197 | 213 | 177 | 196 | 176 | 197 | 179 | 199 | 186 |
| 4. | 200 | 185 | 206 | 182 | 187 | 169 | 191 | 190 | 190 | 179 |
| 5. | 195 | 198 | 210 | 187 | 193 | 178 | 190 | 187 | 193 | 178 |
| Means | 200 | 190 | 206 | 182 | 193 | 180 | 192 | 187 | 193 | 180 |
| Range | 25 | 20 | 30 | 15 | 25 | 30 | 25 | 14 | 20 | 12 |
| S.D. | 10.2 | 7.7 | 10 | 5 | 6.9 | 9.4 | 9.3 | 5.2 | 7.9 | 4.4 |
| % C.V | 5.1 | 4.1 | 4.9 | 2.7 | 3.6 | 5.2 | 4.8 | 2.8 | 4.1 | 2.4 |

As per the results it was observed that same beads are reusable for five times with almost same efficacy.

EXAMPLE X

Stability studies of immobilized microbial beads were carried out by storing the beads in different solutions. The results are presented in Table 6.

TABLE 6

Stability study of immobilized beads stored at different conditions

BOD values (O₂ mg/l) of GGA

| Storage | using beads stored in different solution | | | | |
| --- | --- | --- | --- | --- | --- |
| Time (days) | Distilled Water | 0.1 M CaCl₂ | 0.05 M CaCl₂ | GGA | using Sewage |
| 0 | 178 | 186 | 189 | 171 | 193 |
| 30 | 178 | 184 | 187 | 168 | 190 |
| 60 | 165 | 182 | 185 | 160 | 185 |
| 90 | 166 | 180 | 184 | 161 | 182 |
| 120 | 165 | 175 | 181 | 160 | 180 |
| 150 | 162 | 170 | 174 | 158 | 171 |
| 180 | 155 | 163 | 169 | 149 | 182 |

On storage, it was observed that the beads retained their almost full metabolic activity in 0.05 M CaCl₂ solution.

EXAMPLE XI

Stability studies of immobilized microbial beads were carried out by storing the beads at different temperatures. The results are presented in Table 7.

TABLE 7

Stability study of immobilized beads stored at different temperatures

BOD values (O₂ mg/l) of GGA

| Storage Time (days) | using beads stored in different solution | | | | |
| --- | --- | --- | --- | --- | --- |
|  | 4° C. | 25° C. | 37° C. | 45° C. | using Sewage |
| 0 | 200 | 200 | 200 | 200 | 196 |
| 15 | 196 | 198 | 194 | 193 | 193 |
| 30 | 198 | 196 | 190 | 191 | 195 |
| 60 | 195 | 195 | 187 | 189 | 191 |
| 90 | 199 | 193 | 185 | 184 | 194 |
| 120 | 196 | 189 | 183 | 181 | 191 |
| 150 | 201 | 187 | 180 | 177 | 196 |
| 180 | 198 | 185 | 178 | 172 | 189 |

On storage it was observed that the beds retained their full metabolic activity at 4° C.

From the examples explained above it is clear that BOD values by using immobilized microbial beads were comparable with domestic sewage used as seeding material in conventional BOD test.

ADVANTAGES

1. The prepared immobilized microbial composition (beads) is ready-to-use seed inoculum in BOD test as compared with free microbial composition which needs to be revived one day before the start of BOD test.

2. This immobilized composition is stable and can be reused in BOD analysis.

3. The immobilized microbial composition is more economic than the dehydrated seeding materials due to reusable property.

4. Immobilization of microorganisms leads to a reduction in cell growth and offers a easy to handle and ready-to-use material for many important industrial processes.

5. The advantages of immobilized cells compared to tree cells are, that the immobilized cells can be used repeatedly and with ease of separation.

We claim:

1. An immobilized reusable microbial formulation comprising a synergistic mixture of at least the following isolated bacterial strains present in equal proportion:
   a) *Enterobacter cloaca*
   b) *Citrobacter amalonaticus*
   c) *Pseudomonas aeruginosa*
   d) *Yersinia enterocolitica*
   e) *Klebsiella oxytoca*
   f) *Enterobacter sakazaki* and
   g) *Serratia liquefaciens*.

2. A process for the preparation of immobilized microbial formulation which comprises:
   (a) isolating a range of bacterial strains as claimed in claim 1 from sewage collected from sewage treatment plants;
   (b) culturing the strains on nutrient media to obtain pure cultures;
   (c) testing the individual pure bacterial culture for BOD analysis and recording BOD values obtained from individual strains;

(d) verifying the BOD values obtained with glucose-glutamic acid as a reference standard;

(e) comparing the BOD values using the bacterial strains as seeding material with that of the observed BOD values using domestic sewage as seeding material, collected from sewage treatment plants;

(f) selecting the bacterial strains which have BOD values equal to or more than the BOD values of sewage as observed in step (e);

(g) preparing mixtures of said selected bacterial strains;

(h) testing the mixtures of selected bacterial strains by comparing their BOD values with those of domestic sewage;

(i) selecting the mixtures having optimum BOD values;

(j) inoculating the mixture of said bacterial strains obtained in step (i), individually;

(k) incubating the bacterial strains and growing the incubated strains;

(l) mixing the incubated strains from step (k) in equal proportions on the basis of optical density values;

(m) centrifuging the resultant suspension to obtain pellets, washing the collected pellet with distilled water and suspending the pellet in a solution of an appropriate immobilizing agent;

(n) adding the resultant slurry to an appropriate polymerizing agent to form beads and curing the resultant beads;

(o) hardening the beads by leaving the beads in 0.1 M to 0.2 M $CaCl_2$ solution for approximately 3 hrs.;

(p) storing the prepared immobilized microbial beads in a concentration range of 0.05 M to 0.2 M $CaCl_2$ solution at a temperature preferably less than or equal to 4° C. for longer use;

(q) testing formulated beads for BOD analysis using GGA as a reference standard;

(r) comparing BOD values using the formulated beads with BOD values of those obtained with sewage as seeding material using synthetic samples; and (s) testing the beads for BOD analysis using different industrial samples.

3. A process as claimed in claim 2, wherein the formulated microbial composition is obtained by inoculating a suspension of the bacteria selected from a group consisting of (a) *Enterobacter cloaca* (b) *Citrobacter amalonaticus* (c) *Pseudomonas aeruginosa* (d) *Yersinia enterocolitica* (e) *Klebsiella oxytoca* (f) *Enterobacter sakazaki* and (g) *Serratia liquefaciens*.

4. A process as claimed in claim 2, wherein the individual strains of (a) *Enterobacter cloaca* (b) *Citrobacter amalonaticus* (c) *Pseudomonas aeruginosa* (d) *Yersinia enterocolitica* (e) *Klebsiella oxytoca* (f) *Enterobacter sakazaki* and (g) *Serratia liquefaciens* are inoculated separately in a nutrient broth.

5. A process as claimed in claim 2, wherein the incubation of bacterial strains is carried out by gentle agitation at approximately 75–100 rpm.

6. A process as claimed in claim 2, wherein the growth of incubated bacterial strains is carried out at a temperature ranging between 35° C.–40° C. for a period of 16–24 hours.

7. A process as claimed in claim 2, wherein the said individual strains are mixed in equal proportions.

8. A process as claimed in claim 2, wherein the resultant microbial composition is centrifuged at 8,000 to 12,000 rpm for a period of about 20 to 30 minutes.

9. A process as claimed in claim 2, wherein the resultant pellet is washed by dissolving in distilled water and recentrifuging in the range of 8,000 to 12,000 rpm for a period of about 20 to 30 minutes at a temperature of about 4° C.

10. A process as claimed in claim 2, wherein the resultant pellet obtained is immobilized by entrapping in sodium alginate as an immobilizing agent.

11. A process as claimed in claim 2, wherein the resultant slurry used is pumped into a stirred $CaCl_2$ solution with a concentration ranging between 0.05 to 0.2 M.

12. A process as claimed in claim 2, wherein the slurry is intruded as discrete droplets to form beads.

13. A process as claimed in claim 2, wherein the beads are washed with double distilled water to remove extra $CaCl_2$ solution.

14. A process as claimed in claim 2, wherein the immobilized microbial beads formed are stored in 0.05 M $CaCl_2$ solution at a temperature of about 4° C.

15. A process as claimed in claim 2, wherein the used beads are washed with distilled water.

16. A process as claimed in claim 2, where the beads are stored at about 4° C. for use for at least five times.

* * * * *